United States Patent
Hiroi

(10) Patent No.: US 7,861,590 B2
(45) Date of Patent: Jan. 4, 2011

(54) METHOD OF DETERMINING SUBLIMATE IN THERMOSET FILM WITH QCM SENSOR

(75) Inventor: Yoshiomi Hiroi, Toyama (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 340 days.

(21) Appl. No.: 12/225,474

(22) PCT Filed: Mar. 15, 2007

(86) PCT No.: PCT/JP2007/055240

§ 371 (c)(1),
(2), (4) Date: Sep. 23, 2008

(87) PCT Pub. No.: WO2007/111147

PCT Pub. Date: Oct. 4, 2007

(65) Prior Publication Data

US 2009/0217759 A1    Sep. 3, 2009

(30) Foreign Application Priority Data

Mar. 27, 2006  (JP) .............................. 2006-085602

(51) Int. Cl.
*G01H 13/00*  (2006.01)
*G01N 25/02*  (2006.01)
(52) U.S. Cl. ................. 73/579; 73/25.01; 73/580
(58) Field of Classification Search ............. 73/579, 73/580, 25.01, 25.05
See application file for complete search history.

(56) References Cited

U.S. PATENT DOCUMENTS 6,500,547 B1 * 12/2002 Potyrailo ..................... 428/422
6,706,977 B2 * 3/2004 Cain et al. ............. 177/210 FP
7,036,375 B2 * 5/2006 Nozaki ......................... 73/579
7,662,233 B2 * 2/2010 Sneh ........................... 118/724

(Continued)

FOREIGN PATENT DOCUMENTS

JP       A-06-018394       1/1994

(Continued)

OTHER PUBLICATIONS

Hiroi et al., "New Polymer Platform of BARC for ArF Lithography," *Proceedings of SPIE*, vol. 5753, pp. 655-662, 2005.

*Primary Examiner*—Jacques M Saint Surin
(74) *Attorney, Agent, or Firm*—Oliff & Berridge, PLC

(57) ABSTRACT

A method for measuring an amount of a sublimate in real time with respect to a lapse of heating time, comprising: adhering the sublimate from a thermoset film during heating to a surface of a crystal oscillator using a nozzle inserted into a detection part; and measuring the amount of the sublimate from a change in a resonance frequency corresponding to the amount of the sublimate adhered to the crystal oscillator. In the method, the thermoset film may be formed on a silicon wafer and the measurement is performed while the thermoset film is heated by a heat source disposed under the silicon wafer; or the sublimate may be set so as to flow together with an airstream ascending toward an upper part of an enclosure covering the thermoset film, and the airstream directly contacts the crystal oscillator through the nozzle inserted into the detection part disposed in the path of the airstream.

11 Claims, 7 Drawing Sheets

U.S. PATENT DOCUMENTS

2008/0003837 A1 * 1/2008 Hayasaki et al. ............ 438/758

FOREIGN PATENT DOCUMENTS

| JP | A-06-088795 | 3/1994 | |
| JP | A-08-085721 | 4/1996 | |
| JP | A-10-050673 | 2/1998 | |
| JP | A-2002-048781 | 2/2002 | |
| JP | A-2004-177258 | 6/2004 | |
| JP | 2004184256 | * 7/2004 | |
| JP | A-2005-084621 | 3/2005 | |

* cited by examiner

[FIG. 1]
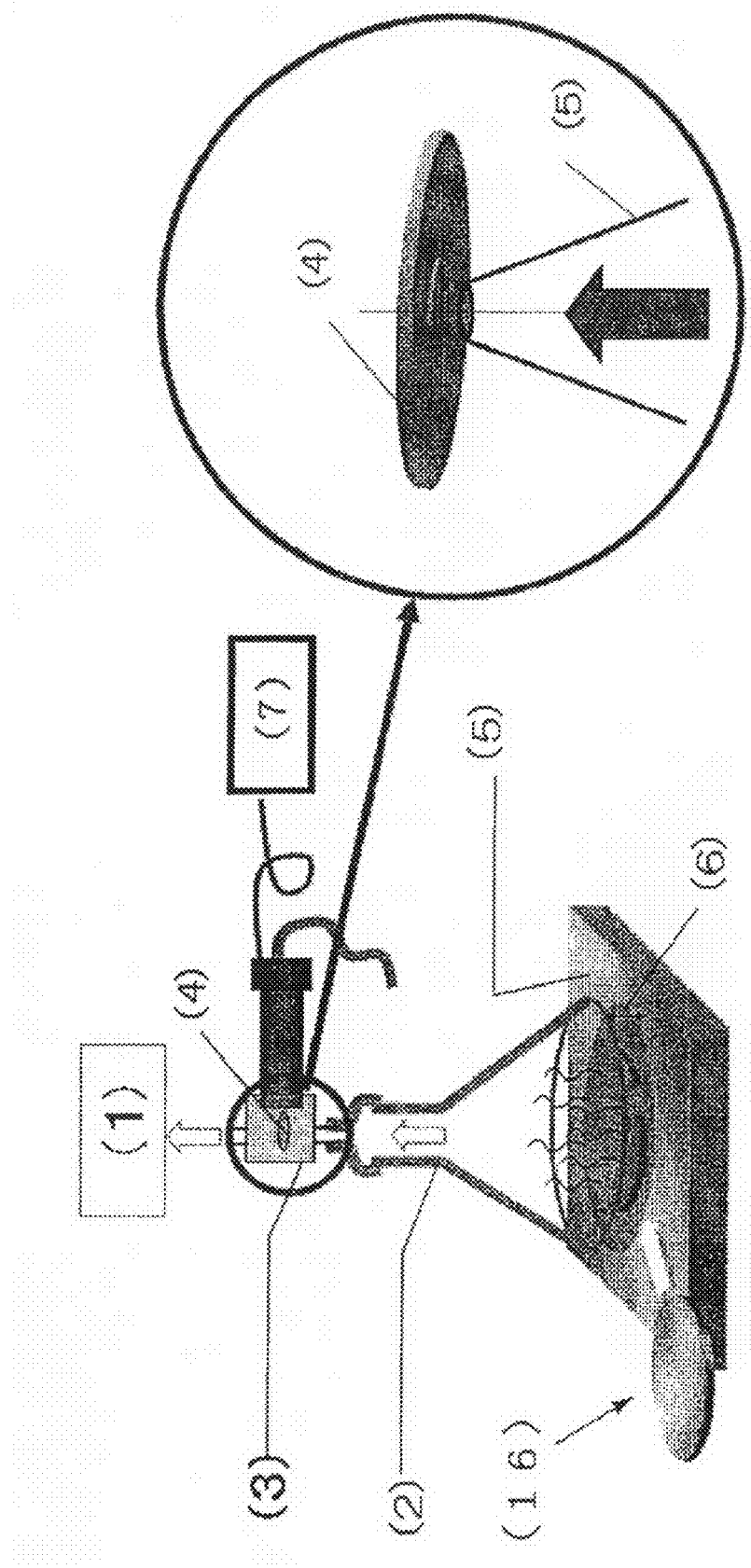

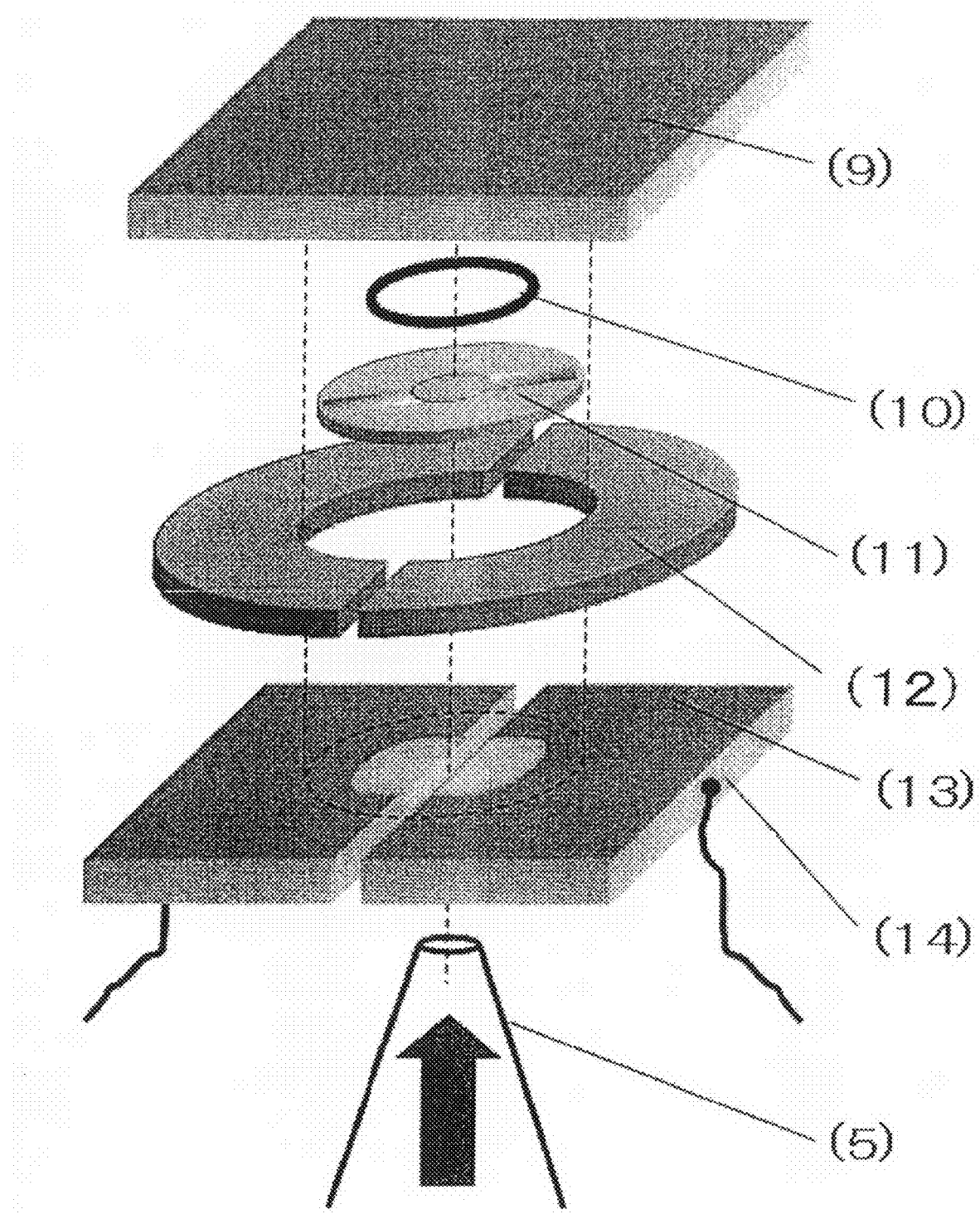
[FIG. 2]

[FIG. 3]
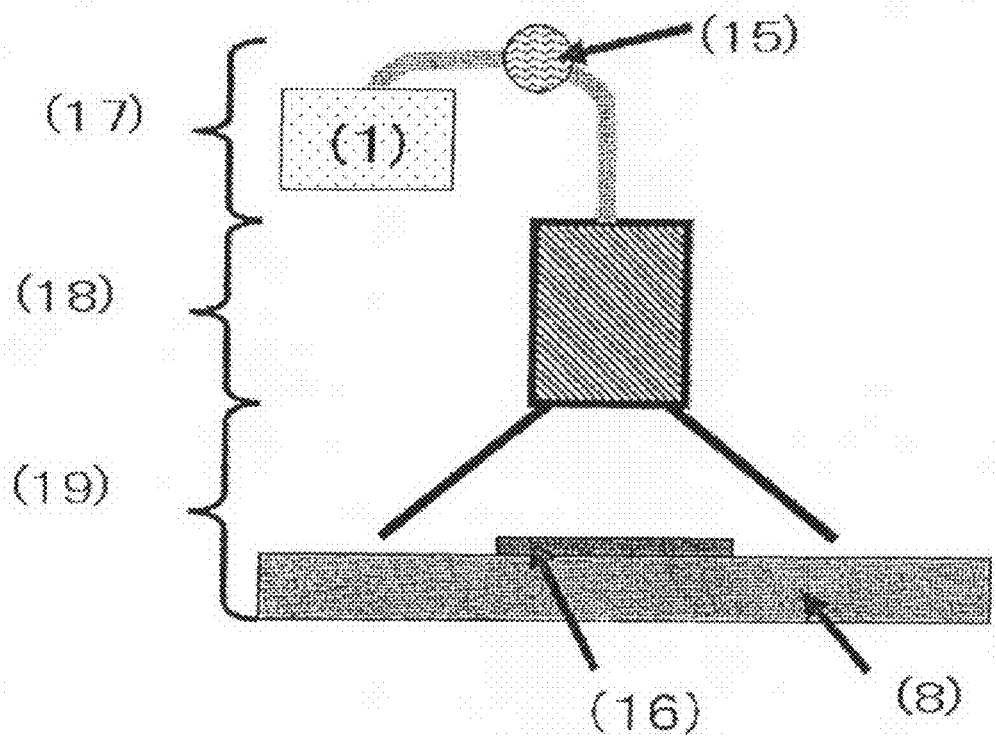
[FIG. 4]
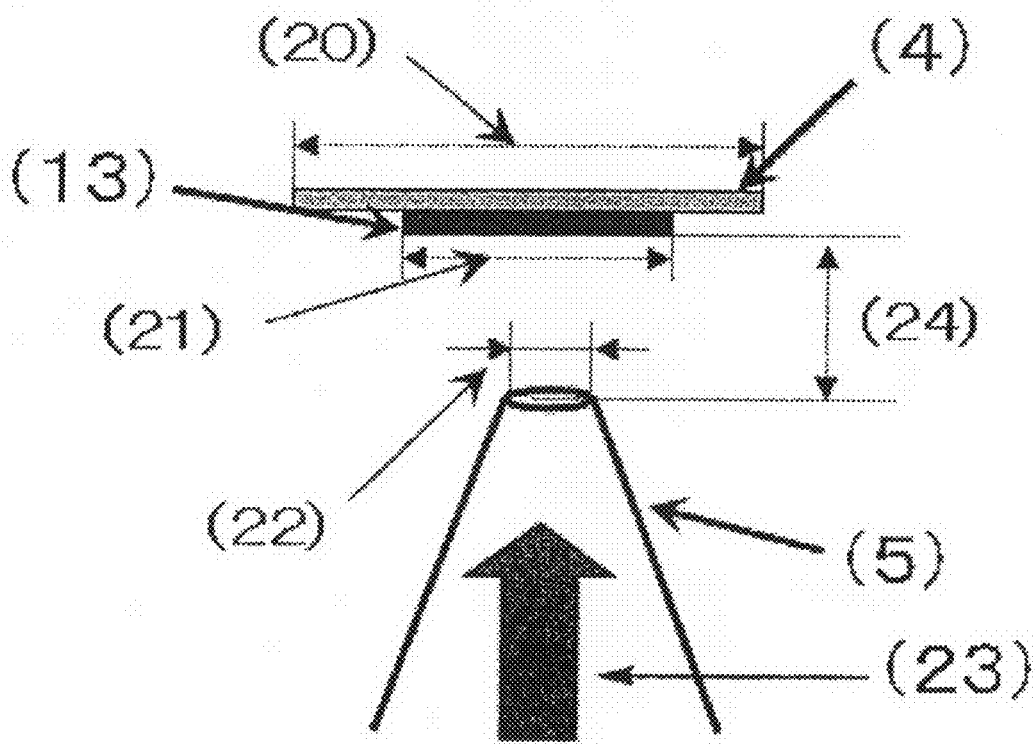

[FIG. 5]
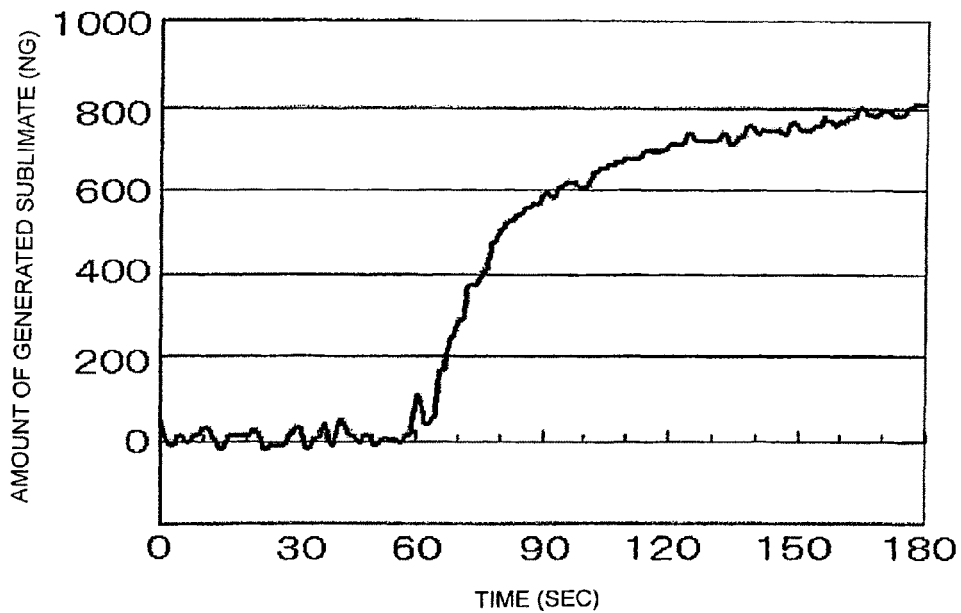
CHANGE WITH TIME IN THE AMOUNT OF GENERATED SUBLIMATE CALCULATED FROM RESONANCE FREQUENCY MEASURED ACCORDING TO THE METHOD OF EXAMPLE 1
[FIG. 6]
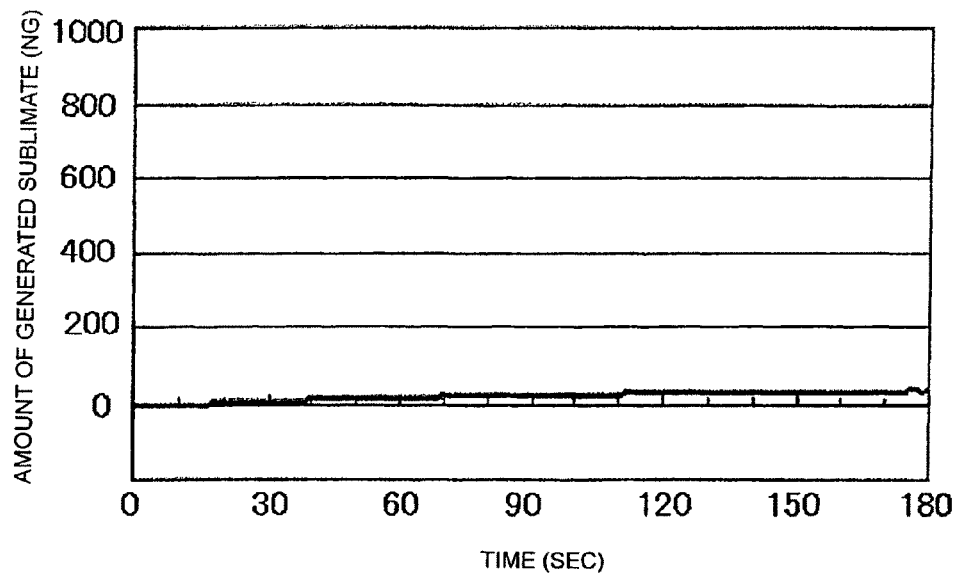
CHANGE WITH TIME IN THE AMOUNT OF GENERATED SUBLIMATE CALCULATED FROM RESONANCE FREQUENCY MEASURED ACCORDING TO THE METHOD OF COMPARATIVE EXAMPLE 1

[FIG. 7]
CHANGE WITH TIME IN THE AMOUNT OF GENERATED SUBLIMATE CALCULATED FROM RESONANCE FREQUENCY MEASURED ACCORDING TO THE METHOD OF COMPARATIVE EXAMPLE 2
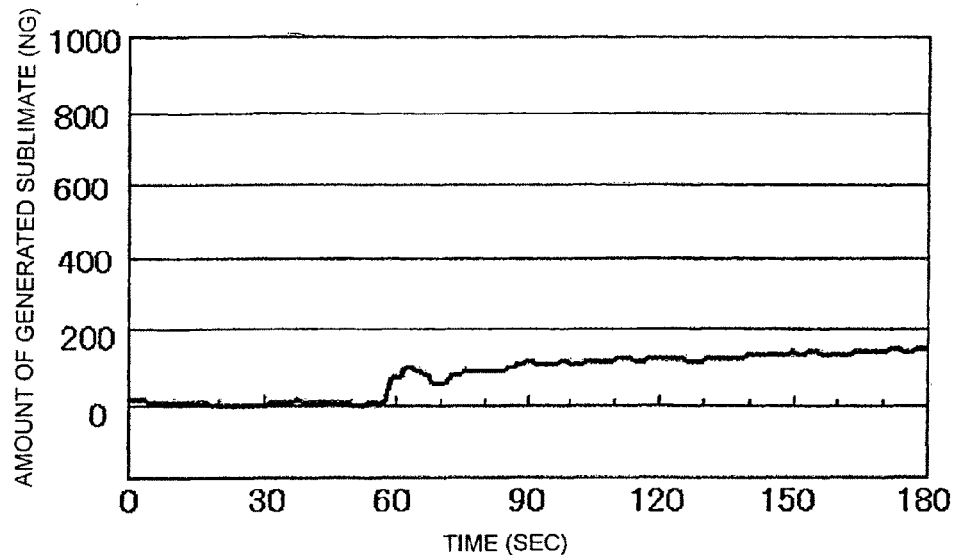
[FIG. 8]
CHANGE WITH TIME IN THE AMOUNT OF GENERATED SUBLIMATE CALCULATED FROM RESONANCE FREQUENCY MEASURED ACCORDING TO THE METHOD OF COMPARATIVE EXAMPLE 3
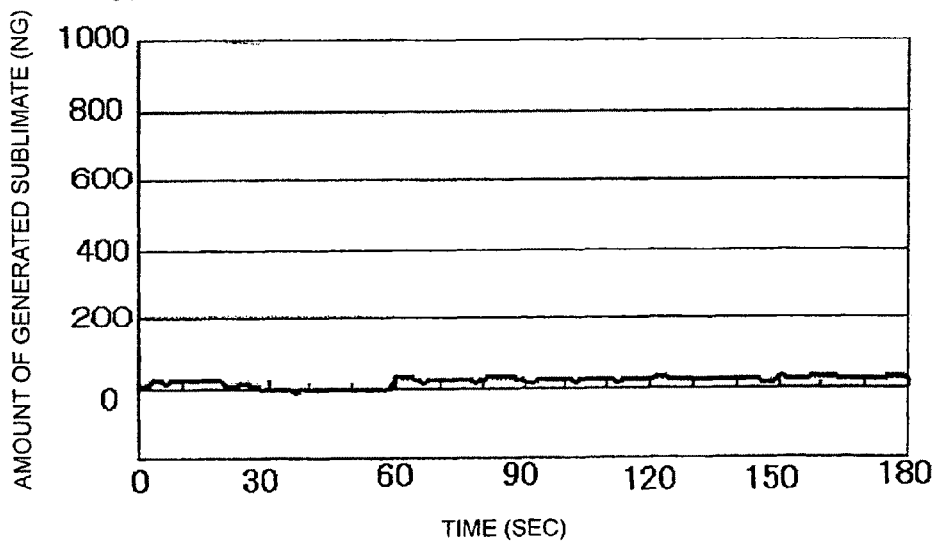

[FIG. 9]
CHANGE WITH TIME IN THE AMOUNT OF GENERATED SUBLIMATE CALCULATED FROM RESONANCE FREQUENCY MEASURED ACCORDING TO THE METHOD OF EXAMPLE 2
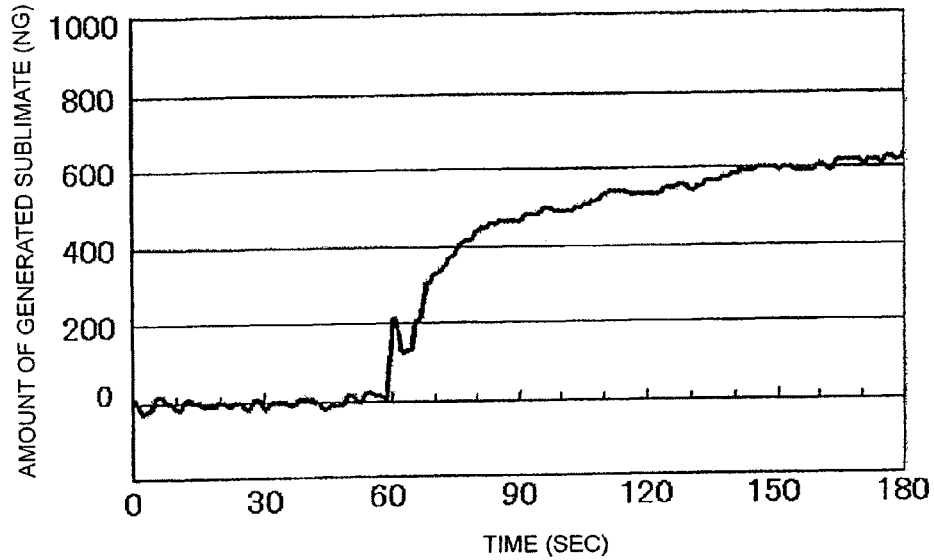
[FIG. 10]
CHANGE WITH TIME IN THE AMOUNT OF GENERATED SUBLIMATE CALCULATED FROM RESONANCE FREQUENCY MEASURED ACCORDING TO THE METHOD OF COMPARATIVE EXAMPLE 4
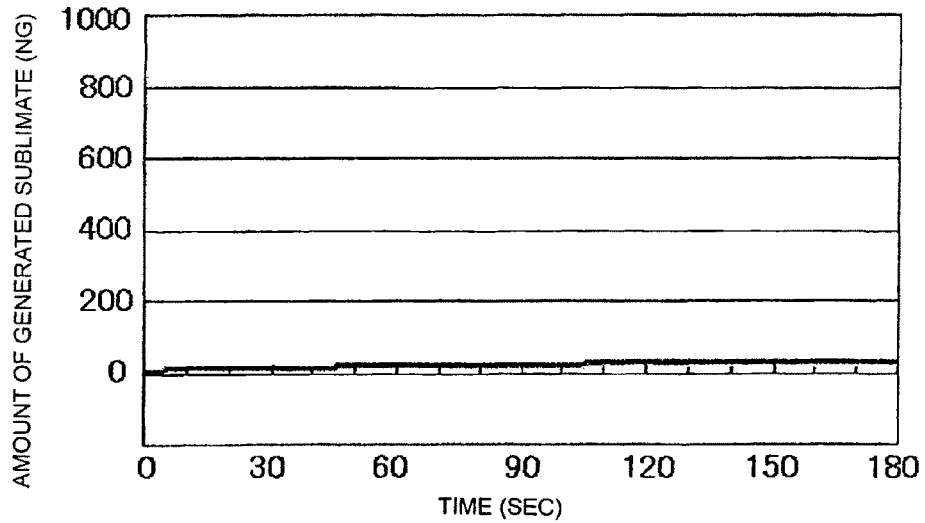

[FIG. 11]
CHANGE WITH TIME IN THE AMOUNT OF GENERATED SUBLIMATE CALCULATED FROM RESONANCE FREQUENCY MEASURED ACCORDING TO THE METHOD OF COMPARATIVE EXAMPLE 5
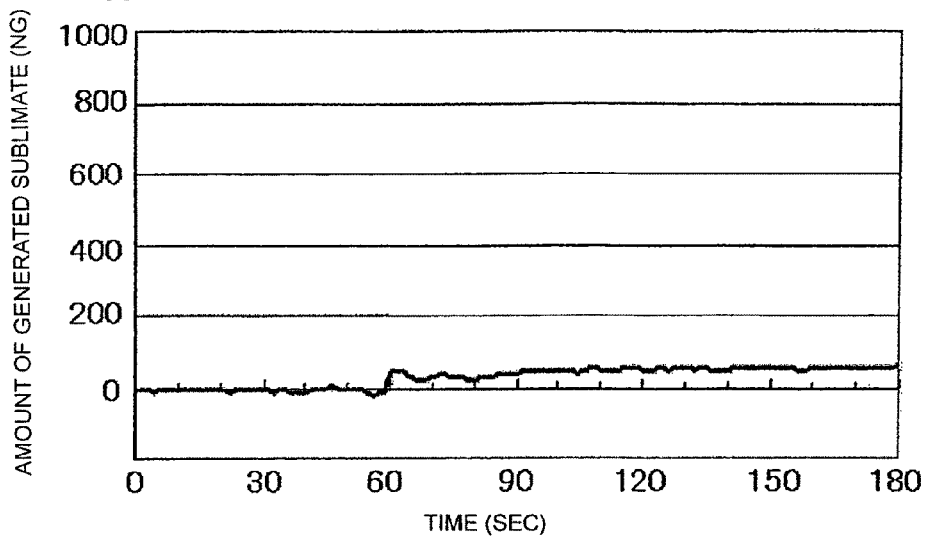
[FIG. 12]
CHANGE WITH TIME IN THE AMOUNT OF GENERATED SUBLIMATE CALCULATED FROM RESONANCE FREQUENCY MEASURED ACCORDING TO THE METHOD OF COMPARATIVE EXAMPLE 6
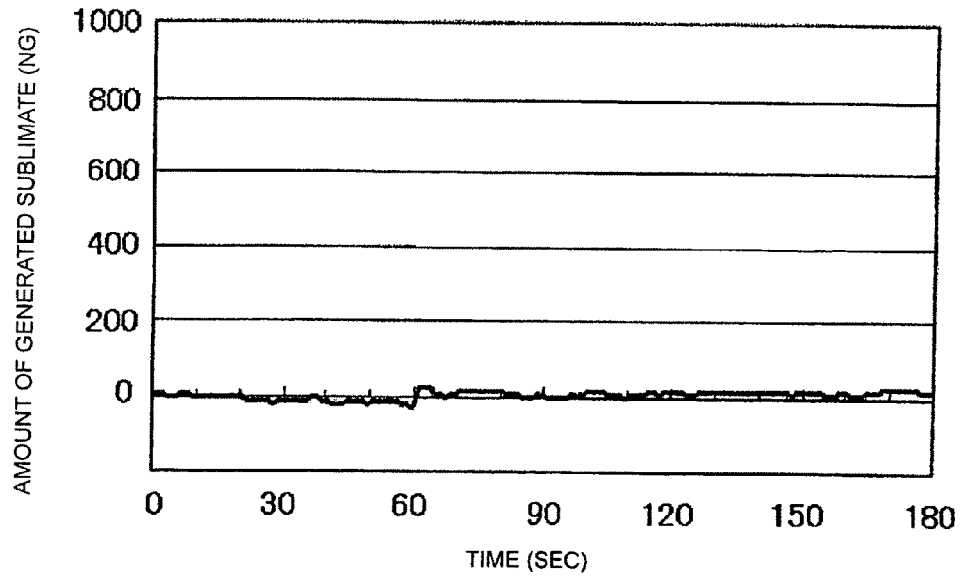

METHOD OF DETERMINING SUBLIMATE IN THERMOSET FILM WITH QCM SENSOR

TECHNICAL FIELD

The present invention relates to a measuring method of a sublimate in a thermoset film using a QCM (Quartz Crystal Microbalance) method.

BACKGROUND ART

A crystal oscillator causes an inverse piezoelectric phenomenon in which the oscillator oscillates when a voltage is applied thereto. It is known that when a substance adheres to a surface of the crystal oscillator, the weight of the crystal oscillator part is changed and the frequency of the crystal oscillator is lowered. A method of measuring the weight of an adhered substance from the change in the frequency is a weight sensor using QCM.

There is disclosed a concentration sensor for detecting a concentration of a substance to be detected in a mixed solution in which a predetermined substance to be detected is dissolved in a predetermined solvent which includes: a crystal oscillator of which natural frequency changes according to the change in the concentration of the substance to be detected; and an oscillating circuit causing the crystal oscillator to oscillate. In the concentration sensor, the crystal oscillator is impregnated with the mixed solution so as to cause the crystal oscillator to oscillate and the natural frequency of the crystal oscillator at this time is obtained. As a result, the concentration of the substance to be detected in the mixed solution is obtained (Patent Document 1).

There is disclosed a detecting sensor in which a cyclodextrin derivative, which is combined with a specific substance, is fixed to an electrode provided in the crystal oscillator. The cyclodextrin derivative is fixed by a disulfide compound or a thiol compound (Patent Document 2).

There is described that using a QCM sensor, sublimates in some types of lower layer antireflection film were determined quantity under the heating at 200° C. and compared. It is reported that in measuring the sublimate of an antireflection film applied to a 4 inches wafer, the difference between the materials could be confirmed by baking and measuring dozens of wafers (Non-Patent Document 1).

Patent Document 1: Japanese Patent Application Publication No. JP-A-6-18394 (claims)

Patent Document 2: Japanese Patent Application Publication No. JP-A-2004-177258 (claims)

Non-Patent Document 1: SPIE Vol. 5753, pp. 655-662 (2005)

DISCLOSURE OF THE INVENTION

Problems to be Solved by the Invention

The present invention relates to a sensor for determining the amount of a sublimate by a method in which a sublimate in a thermoset film is adhered to the surface of a crystal oscillator and the electric resonance frequency is changed due to the piezoelectric properties of the oscillator, so that the amount of the adhered sublimate is determined quantity from this change in the frequency.

In a lithography process in the production of a semiconductor, there is a process in which a semiconductor substrate is coated with a photoresist and the semiconductor substrate is processed by a resist pattern obtained by exposing through a photo mask.

For preventing the diffuse reflection from a semiconductor substrate during the exposure of the photoresist, methods for forming an antireflection film as a layer under the photoresist are performed. In these methods, a semiconductor substrate is coated with a composition for forming an antireflection film by a spin coating method and is cured by heating to obtain the antireflection film. Generally, the composition for forming an antireflection film contains resin components, light absorbing group components, additive components and solvent components and these components are cured by heating to produce the antireflection film. However, these components in the composition for forming an antireflection film during heating sometimes scatter a sublimate into air as themselves or as reaction products. When the sublimate is discharged from the chamber to the outside by suction, a phenomenon sometimes occurs that the sublimate adheres to the inside of the chamber and with the passage of time falls onto an antireflection film formed on a semiconductor substrate. A falling matter of such an adhered substance becomes a foreign matter that leads to hindrance or error during the lithography process. Similarly, when the surface of a formed antireflection film is coated with a composition for forming photoresist and is converted into a photoresist film by heating, there are some cases in which components or reaction products are scattered out of the photoresist film into air as sublimates which become adhered substances and the adhered substances fall onto the photoresist film to become foreign matters which lead to the cause of hindrance or error.

In a process where a semiconductor having a wiring width of several tens of nm is processed, even a trace amount of falling matters may cause a wire break or a short circuit at a part onto which the falling matter has fallen, which is a problem.

The sublimates causing the falling matters are not considered to be not low molecular weight components such as solvent components, but are considered to be components having a molecular weight distribution and a relatively high molecular weight such as resin components, light absorbing group components, additive components, and reaction products thereof.

For preventing such a problem beforehand, it is considered to be beneficial in developing a composition for forming an antireflection film or a composition for forming a resist film which generates no sublimate or a slight amount of sublimate, if the presence or absence or the amount of sublimated components generated during thermosetting a thermoset film, such as, in particular, a composition for forming an antireflection film or a composition for forming a resist film, can be measured.

Further, detecting the amount of the sublimate that is generated with respect to a lapse of heating time is considered to be beneficial in investigating a temperature elevating process in which the sublimate is unlikely to be generated when a composition for forming an antireflection film or a composition for forming a resist film is coated and thermoset by heating.

The present invention provides a method for solving these problems.

Means for Solving the Problem

According to a first aspect of the present invention, a method for measuring an amount of a sublimate in real time with respect to a lapse of heating time includes adhering the sublimate from a thermoset film during heating to a surface of a crystal oscillator using a nozzle inserted into a detection part and measuring the amount of the sublimate from a change in a resonance frequency corresponding to the amount of the sublimate adhered to the crystal oscillator;

according to a second aspect, in the method according to the first aspect, the thermoset film is formed on a silicon wafer and the measurement is performed while the thermoset film is heated with a heat source disposed under the silicon wafer;

according to a third aspect, in the method according to the first or second aspect, the sublimate is set so as to flow together with an airstream ascending toward an upper part in an enclosure covering the thermoset film and the airstream directly contacts the crystal oscillator through the nozzle inserted into the detection part disposed in the path of the airstream;

according to a fourth aspect, in the method according to any one of the first to third aspects, the airstream is generated by the suction of a pump and a flow rate thereof is 0.01 to 20.0 m$^3$/s;

according to a fifth aspect, in the method according to any one of the first to fourth aspects, the nozzle inserted into the detection part has a nozzle aperture smaller than the diameter of a sensor and a distance between the nozzle and the sensor is shorter than the diameter of the sensor;

according to a sixth aspect, in the method according to any one of the first to fifth aspects, the heat source is that controlled to temperatures of 100 to 400° C. by a hot plate;

according to a seventh aspect, in the method according to any one of the first to sixth aspects, the surface of the crystal oscillator is coated with the same material as a surface material of the enclosure covering the thermoset film or with a coating material forming the thermoset film;

according to an eighth aspect, in the method according to the seventh aspect, the coating of the surface of the crystal oscillator is a compound containing silicon and aluminum;

according to a ninth aspect, in the method according to any one of the first to the eighth-aspects, the crystal oscillator is used at a resonance frequency ranging from 100 Hz to 100 MHz;

according to a tenth aspect, in the method according to any one of the first to ninth aspects, the thermoset film is an antireflection film used as an under layer of a photoresist used in a lithography process for producing a semiconductor device; and according to an eleventh aspect, an apparatus for measuring a sublimate from a thermoset film utilizing the method described in any one of the first to tenth aspects.

Effects of the Invention

Since the presence or absence or the amount of the sublimate components generated when thermosetting a thermoset film, particularly a composition for forming an antireflection film or a composition for forming a resist film on a semiconductor substrate can be more accurately detected, the development of a composition for forming an antireflection film or a composition for forming a resist film which generate no sublimate or a slight amount of sublimate can be performed.

Further, it is possible to investigate a temperature elevating process in which the sublimate is unlikely to be generated when a composition for forming an antireflection film or a composition for forming a resist film is coated and is thermoset by the heating, due to detection of the amount of the sublimate that is generated with respect to a lapse of heating time.

BRIEF DESCRIPTION OF THE DRAWINGS

FIG. 1 is a view showing an overall configuration of an apparatus for measuring a sublimate from a thermoset film.

FIG. 2 is an enlarged view of a detection part of the measuring apparatus shown in FIG. 1.

FIG. 3 is a schematic view of the whole apparatus for measuring the sublimate from the thermoset film.

FIG. 4 is a view showing the detection part of the apparatus for measuring the sublimate from the thermoset film.

FIG. 5 is a graph showing a change with time in the amount of the generated sublimate calculated from a resonance frequency measured according to the method of Example 1.

FIG. 6 is a graph showing the change with time in the amount of the generated sublimate calculated from the resonance frequency measured according to the method of Comparative Example 1.

FIG. 7 is a graph showing the change with time in the amount of the generated sublimate calculated from the resonance frequency measured according to the method of Comparative Example 2.

FIG. 8 is a graph showing the change with time in the amount of the generated sublimate calculated from the resonance frequency measured according to the method of Comparative Example 3.

FIG. 9 is a graph showing the change with time in the amount of the generated sublimate calculated from the resonance frequency measured according to the method of Example 2.

FIG. 10 is a graph showing the change with time in the amount of the generated sublimate calculated from the resonance frequency measured according to the method of Comparative Example 4.

FIG. 11 is a graph showing the change with time in the amount of the generated sublimate calculated from the resonance frequency measured according to the method of Comparative Example 5.

FIG. 12 is a graph showing the change with time in the amount of the generated sublimate calculated from the resonance frequency measured according to the method of Comparative Example 6.

In the figures, reference numeral (1) denotes a pump. (2) denotes an enclosure covering in a triangle funnel shape (collecting funnel). (3) denotes a flow attachment (detection part). (4) denotes a QCM sensor. (5) denotes a nozzle. (6) denotes a gas inflow opening between the enclosure covering in a triangle funnel shape and a hot plate. (7) denotes a personal computer. (8) denotes the hot plate. (9) denotes a top board. (10) denotes an O-ring. (11) denotes a crystal oscillator. (12) denotes a guide. (13) denotes a base substrate. (14) denotes an electrode. (15) denotes a flow rate controller. (16) denotes a wafer coated with a substance to be measured. (17) shows the position of a pump unit in the overall configuration. (18) shows the position of the flow attachment in the overall configuration. (19) shows the position of a chamber unit in the overall configuration. (20) shows the diameter of the crystal oscillator. (21) shows the diameter of the electrode. (22) shows the aperture of the nozzle. (23) shows the airstream. (24) shows the distance between the nozzle and the sensor.

BEST MODES FOR CARRYING OUT THE INVENTION

The present invention is a method for measuring an amount of a sublimate with respect to a lapse of heating time. The method includes: adhering a sublimate from a thermoset film during heating to a surface of a crystal oscillator; and measuring the amount of the sublimate from the change in the resonance frequency of the crystal oscillator corresponding to the amount of the sublimate adhered to the crystal oscillator.

The thermoset film used in the present invention is obtained by thermosetting a composition for forming a thermoset film containing a thermoset compound and a solvent. The thermoset film can optionally contain a light absorbing compound and an additive component. The additive component can contain crosslinkable compounds, acids, acid generating agents, rheology controlling agents, and surfactants. The ratio of the solid content in the composition for forming a thermoset film used in the present invention is not particularly limited so long as each component is homogeneously dissolved in a solvent, but is 1 to 50% by mass, or 1 to 30% by mass, or 1 to 25% by mass, for example. Here, the solid content means a content calculated by subtracting the content of solvent components from the content of all components of the composition for forming a thermoset film.

As the thermoset compound, thermoset monomers, thermoset resins or mixtures thereof are used. The thermoset compound is not limited so long as it is a component capable of being cured by heating. When crosslinkable groups such as hydroxyl groups, epoxy groups and carboxyl groups within the molecule are reacted with each other, crosslinking reaction occurs so that the thermoset compound can be cured.

Examples of the thermoset compound include vinyl phenols and polymers thereof, compounds containing a unit structure having hydroxyl group-containing maleimide derivatives and polymers thereof, tris-(2,3-epoxypropyl)-isocyanurate and polymers thereof, tris-(2-hydroxyethyl)-isocyanurate and polymers thereof, hydroxyl group-containing halogenated bisphenol A-based resins, polymers of compounds containing a unit structure having lactones with hydroxyalkyl methacrylates (in which the alkyl group has a carbon number of 1 to 4), hydroxybenzyl methacrylates and polymers thereof, phenol novolak resins, cresol novolak resins, naphthalene novolak resins, polymers of compounds containing a unit structure having norbornenes with hydroxyalkyl methacrylates (in which the alkyl group has a carbon number of 1 to 4), polymers of compounds containing a unit structure having epoxy groups with compounds containing a unit structure having phenolic hydroxyl groups, carboxyl groups or protected carboxyl groups, hydroxyl group-containing acrylic ester polymers, polymers of glycidyl methacrylates with acrylic esters, reaction products of poly(amic acids) with epoxy group-containing compounds, monoallyl isocyanuric acid-based polymers, reaction products of glycidyl isocyanulates with hydroxyl group-containing benzoic acid, reaction products of maleic acid or fumaric acid with epoxy compounds, and mixtures of compounds having a fluorene structure and phenol novolak resins.

These thermoset monomers and thermoset resins can be used as those having molecular weight of 100 to 1,000,000. These monomers and resins have a weight average molecular weight of, for example, 1,000 to 200,000 or, for example, 3,000 to 100,000, 4,000 to 30,000, or 5,000 to 25,000. The ratio of the thermoset monomers and thermoset resins in the solid content are, for example, 50 to 99% by mass, or 60 to 99% by mass.

The solvent for the composition for forming a thermoset film used in the present invention can be used without particular limitation so long as the solvent is a solvent capable of dissolving the solid content. Examples of such a solvent include ethylene glycol monomethyl ether, ethylene glycol monoethyl ether, methyl cellosolve acetate, ethyl cellosolve acetate, diethylene glycol monomethyl ether, diethyleneglycol monoethyl ether, propylene glycol, propylene glycol monomethyl ether, propylene glycol monomethyl ether acetate, propylene glycol propyl ether acetate, toluene, xylene, methyl ethyl ketone, cyclopentanone, cyclohexanone, ethyl 2-hydroxy propionate, ethyl 2-hydroxy-2-methyl propionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate and butyl lactate. These solvents may be used individually or in combination of two or more types thereof. Further, high boiling point solvents such as propylene glycol monobutyl ether and propylene glycol monobutyl ether acetate may be incorporated in the solvent to be used.

The crosslinkable compound capable of being arbitrary added to the composition for forming the thermoset film used in the present invention is not particularly limited, however, a crosslinkable compound having at least two crosslinkage-forming substituents is preferably used. For example, a compound having 2 or more, for example, 2 to 6 crosslinkable groups such as isocyanate groups, epoxy groups, hydroxymethylamino groups and alkoxymethylamino groups can be used.

Examples of the crosslinkable compound include nitrogen-containing compounds having 1 to 6, or 2 to 4 nitrogen atom(s) substituted with alkoxymethyl groups such as methylol groups or methoxymethyl groups, ethoxymethyl groups, butoxymethyl groups, and hexyloxymethyl groups. Specific examples thereof include nitrogen-containing compounds such as hexamethoxymethyl melamine, tetramethoxymethyl benzoguanamine, 1,3,4,6-tetrakis(methoxymethyl)glycoluryl, 1,3,4,6-tetrakis(butoxymethyl)glycoluryl, 1,3,4,6-tetrakis(hydroxymethyl)glycoluryl, 1,3-bis(hydroxymethyl)urea, 1,1,3,3-tetrakis(butoxymethyl)urea, 1,1,3,3-tetrakis(methoxymethyl)urea, 1,3-bis(hydroxymethyl)-4,5-dihydroxy-2-imidazoline and 1,3-bis(methoxymethyl)-4,5-dimethoxy-2-imidazolinone. Examples of the crosslinkable compound further include commercially available nitrogen-containing compounds such as compounds manufactured by Mitsui Cytec Ltd., for example, methoxymethyl type melamine compounds (trade names: Cymel 300, Cymel 301, Cymel 303, Cymel 350), butoxymethyl type melamine compounds (trade names: MYCOAT 506, MYCOAT 508), glycoluryl compounds (trade names: Cymel 1170, Powderlink 1174), methylated urea resins (trade name: UFR65), butylated urea resins (trade names: UFR300, U-VAN10S60, U-VAN10R, U-VAN 11HV), and compounds manufactured by DIC Corporation, for example, urea/formaldehyde-based resins (trade name: Beckamine J-300S, Beckamine P-955, Beckamine N). In addition, as the crosslinkable compound, polymers produced using acrylamide compounds or methacrylamide compounds substituted with hydroxymethyl groups or alkoxymethyl groups such as N-hydroxymethylacrylamide, N-methoxymethylmethacrylamide, N-ethoxymethylacrylamide and N-butoxymethylmethacrylamide can be used. Examples of such polymers include copolymers of poly(N-butoxymethylacrylamide), N-butoxymethylacrylamide and styrene, copolymers of N-hydroxymethylmethacrylamide and methyl methacrylate, copolymers of N-ethoxymethylmethacrylamide and benzyl methacrylate, and copolymers of N-butoxymethylacrylamide, benzyl methacrylate and 2-hydroxypropyl methacrylate.

The content of the crosslinkable compound in the solid content is, for example, 1 to 50% by mass, or 10 to 40% by mass.

The composition for forming the thermoset film used in the present invention can contain acid compounds. Examples of the acid compound include: sulfonic acid compounds such as p-toluenesulfonic acid, trifluoromethanesulfonic acid, pyridinium-p-toluenesulfonic acid, salicylic acid, camphorsulfonic acid, sulfosalicylic acid, 4-chlorobenzenesulfonic acid, 4-hydroxybenzenesulfonic acid, benzenedisulfonic acid, 1-naphthalenesulfonic acid and pyridinium-1-naphthalenesulfonic acid; and carboxylic compounds such as salicylic acid, sulfosalicylic acid, citric acid, benzoic acid and hydroxybenzoic acid. In addition, examples of the acid compound include acid-generating agents generating acids by heat or light such as 2,4,4,6-tetrabromocyclohexadienone, benzoin tosylate, 2-nitrobenzyl tosylate, bis(phenylsulfonyl) diazomethane, p-trifluoromethylbenzenesulfonic acid-2,4-dinitrobenzyl, phenyl-bis(trichloromethyl)-s-triazine and N-hydroxysuccinimide trifluoromethanesulfonate. Examples of the acid compound also include: iodonium salt-based acid generating agents such as diphenyliodonium hexafluorophosphate, diphenyliodonium trifluoromethanesulfonate, diphenyliodonium nonafluoro-n-butanesulfonate, diphenyliodonium perfluoro-n-octanesulfonate, diphenyliodonium camphorsulfonate, bis(4-tert-butylphenyl)iodonium camphorsulfonate and bis(4-tert-butylphenyl)iodonium tri-fluoromethanesulfonate; sulfonium salt-based acid generating agents such as triphenylsulfonium hexafluoroantimonate, triphenylsulfonium nonafluoro-n-butanesulfonate, triphenylsulfonium camphorsulfonate and triphenylsulfonium trifluoromethanesulfonate; and sulfonimide compound-based acid generating agent such as N-(trifluoromethanesulfonyloxy)succinimide, N-(nonafluoro-n-butanesulfonyloxy)succinimide, N-(camphorsulfonyloxy)succinimide and N-(trifluoromethanesulfonyloxy)naphthalimide. As the acid compound, sulfonic acid compounds, iodonium salt-based acid generating agents, sulfonium salt-based acid generating agents or sulfonimide compound-based acid generating agents are preferably used. The acid compounds may be used individually or in combination of two or more types thereof. For example, as the acid compound, sulfonic acid compounds alone can be used. In addition, as the acid compound, a combination of sulfonic acid compounds and iodonium salt-based acid generating agents, or a combination of sulfonic acid compounds and sulfonium salt-based acid generating agents, or a combination of sulfonic acid compounds and sulfonimide compound-based acid generating agents, can be used. The content of the acid compound or the acid generating agent in the solid content is, for example, 0.1 to 10% by mass or 0.1 to 5% by mass.

When used in the antireflection film, the light absorbing compound can be used without particular limitations so long as it has high absorbing power for a light in a photosensitivity wavelength region of photosensitive components in the photoresist disposed on the antireflection film. For example, as the light absorbing compound, benzophenone compounds, benzotriazole compounds, azo compounds, naphthalene compounds, anthracene compounds, anthraquinone compounds, triazine compounds, triazine-trione compounds and quinoline compounds and the like, can be used. Naphthalene compounds, anthracene compounds, triazine compounds and triazine-trione compounds are used. Specific examples thereof include 1-naphthalene-carboxylic acid, 2-naphthalene-carboxylic acid, 1-naphthol, 2-naphthol, naphthylacetatic acid, 1-hydroxy-2-naphthalene-carboxylic acid, 3-hydroxy-2-naphthalene-carboxylic acid, 3,7-dihydroxy-2-naphthalene-carboxylic acid, 6-bromo-2-hydroxynaphthalene, 2,6-naphthalene-dicarboxylic acid, 9-anthracene-carboxylic acid, 10-bromo-9-anthracene-carboxylic acid, anthracene-9,10-dicarboxylic acid, 1-anthracene-carboxylic acid, 1-hydroxyanthracene, 1,2,3-anthracene-triol, 9-hydroxymethyl-anthracene, 2,7,9-anthracene-triol, benzoic acid, 4-hydroxybenzoic acid, 4-bromobenzoic acid, 3-iodobenzoic acid, 2,4,6-tribromophenol, 2,4,6-tribromoresorcinol, 3,4,5-triiodobenzoic acid, 2,4,6-triiodo-3-aminobenzoic acid, 2,4,6-triiodo-3-hydroxybenzoic acid and 2,4,6-tribromo-3-hydroxybenzoic acid. When the light absorbing compound is used, the used amount thereof in the solid content is, for example, 0.1 to 40% by mass.

Examples of the rheology controlling agent include: phthalic acid compounds such as dimethyl phthalate, diethyl phthalate, diisobutyl phthalate, dihexyl phthalate and butylisodecyl phthalate; adipic acid compounds such as di-n-butyl adipate, diisobutyl adipate, diiosoctyl adipate and octyldecyl adipate; maleic acid compounds such as di-n-butyl maleate, diethyl maleate and dinonyl maleate; oleic acid compounds such as methyl oleate, butyl oleate and tetrahydrofurfuryl oleate; and stearic acid compounds such as n-butyl stearate and glyceryl stearate. When the rheology controlling agent is used, the used amount thereof in the solid content is, for example, 0.001 to 10% by mass.

Examples of the surfactant include: polyoxyethylene alkyl ethers such as polyoxyethylene lauryl ether, polyoxyethylene stearyl ether, polyoxyethylene cetyl ether and polyoxyethylene oleyl ether; polyoxyethylene alkylallyl ethers such as polyoxyethylene octylphenol ether and polyoxyethylene nonylphenol ether; polyoxyethylene-polyoxypropylene block copolymers; sorbitan fatty acid esters such as sorbitan monolaurate, sorbitan monopalmitate, sorbitan monostearate, sorbitan monooleate, sorbitan trioleate and sorbitan tristearate; nonion type surfactant such as polyoxyethylenesorbitan fatty acid esters, for example, polyoxyethylenesorbitan monolaurate, polyoxyethylenesorbitan monopalmitate, polyoxyethylenesorbitan monostearate, polyoxyethylenesorbitan trioleate and polyoxyethylenesorbitan tristearate; fluorine-based surfactants such as trade names Eftop EF301, EF303 and EF352 (manufactured by Jemco Inc.), trade names Megafac F 171, F 173, R-08 and R-30 (manufactured by DIC Corporation), trade names Fluorad FC430 and FC431 (manufactured by Sumitomo 3M Limited), and trade names Asahi guard AG710, Surfron S-382, SC101, SC102, SC 103, SC104, SC105 and SC106 (manufactured by Asahi Glass Co., Ltd.); and organosiloxane polymer KP341 (manufactured by Shin-Etsu Chemical Co., Ltd.). These surfactants may be used individually or in combination of two or more types thereof. When the surfactant is used, the used amount thereof in the solid content is, for example, 0.0001 to 5% by mass.

Hereinafter, the thermoset film is described as an antireflection film used in a lithography process for producing a semiconductor device.

The measuring apparatus in which the measuring method of the present invention is embodied, is formed mainly from a chamber unit capable of covering and enclosing a sublimate generated by baking an antireflection film on a wafer (substrate), a flow attachment for adhering efficiently the sublimate to a QCM sensor, and a pump unit for generating an airstream and for controlling the flow rate of the airstream. These three units are linked to each other in an airtight state and the sublimate generated in the chamber unit is sucked by the pump unit through the flow attachment and is allowed to successively flow together with the airstream. The flow attachment is a detection part which is a unit containing a QCM sensor in which an electrode is attached to a crystal oscillator and a nozzle disposed under the QCM sensor. When the airstream from the nozzle, which contains the sublimate, contacts the sensor, the sublimate adheres to the surface of the sensor and the airstream flows beyond the sensor into the pump unit.

The chamber unit is formed mainly from two parts such as a hot plate and an enclosure over the hot plate to which airtightness is imparted. These parts are processed into a shape suitable for generating the sublimate from a silicon wafer having a size of 4 inches to 16 inches or a coated substrate. The hot plate in the chamber unit heats the thermoset film on the wafer to a temperature of 100 to 400° C. and the sublimate generated from the thermoset film is measured, in which the thermoset film is maintained at an arbitrarily-set constant temperature in a range of 100 to 400° C. by the hot plate during one measurement. The enclosure part (collecting funnel) of this chamber has preferably a small surface area for efficiently collecting the sublimate and for preventing the sublimate from adhering to the surface thereof. As the chamber, for example, a body in a triangle funnel-shape is considered.

As a method for installing a coated substrate in the chamber unit before the measurement, an installing method in a sliding mode is preferred for suppressing a temperature deviation due to a thermal change. In other words, it is preferred to suppress the time of opening-closing the chamber to the minimum, and is more preferred to perform the measurement without opening-closing the chamber. For example, such a method can be considered that as a sliding aperture for the installation of the substrate, a slit is formed beforehand in the chamber enclosure and the hot plate, and a wafer coated with an antireflection film is introduced therethrough.

In addition, it is important to impart the airtightness to the above three units. However, for generating the flow of the airstream, a slit for causing the airstream to flow in is necessary to be provided between the hot plate and the enclosure part of the chamber unit, separately from the sliding aperture for the installation. The slit (gas inflow aperture) for generating the airstream and for causing gas to flow in is provided as an aperture part of around 1 to 5 mm, preferably of around 2 mm from the surface of the hot plate. Examples of the gas flowing in to become the airstream include air and an inert gas (nitrogen, argon and helium), but air is preferred.

The flow attachment part is formed mainly from the QCM sensor, the nozzle for adhering the sublimate directly to the sensor, and the enclosure for enclosing the above parts and of which airtightness is taken into consideration. When flowing into the flow attachment from the chamber unit, the sublimate is sprayed via the nozzle against the QCM sensor and does not flow into the flow attachment through a path other than the nozzle.

The apparatus of the present invention is characterized by being capable of measuring with high sensitivity. In the apparatus according to the measuring method of the present invention, a relative difference in size between an antireflection film to be measured (subject to be measured) and an antireflection film which is the standard (reference) can be measured by the weight, even when the wafer to be measured is only one piece. Therefore, the difference between the materials can be confirmed. As a necessary factor for this, the presence of a nozzle for adhering the airstream directly to the sensor or a portion for narrowing the airstream to the sensor corresponding to the nozzle is essential. As a requirement for the nozzle, such conditions are essential that the aperture of the nozzle is smaller than the diameter of the sensor and the distance between the nozzle and the sensor is smaller than the diameter of the sensor. By satisfying these conditions, a measurement of the amount of the sublimate with high sensitivity becomes possible. Here, the diameter of the sensor means the diameter of the crystal oscillator.

The larger the resonance frequency of the crystal oscillator is, the higher the resolution thereof is but the larger the noise becomes. Therefore, in general, a sensor having a resonance frequency of preferably around 100 Hz to 100 MHz, more preferably around 1 MHz to 30 MHz is preferred. Here, this value corresponds to the thickness of the crystal piece and the thinner the thickness is, the higher the resonance frequency is. When the change in the frequency is large, the sensor has high resolution.

The smaller the electrode size of the crystal oscillator is, the higher the sensitivity thereof is. The larger the electrode size of the crystal oscillator is, the smaller the noise thereof is. Therefore, the electrode size of around 0.1 mm to 100 mm is generally known and that of around 1 mm to 10 mm is preferred for the apparatus of the present invention.

In addition, examples of the electrode material include: conductive metals such as gold, copper, silver, iron, aluminum, titanium, chromium, mixtures of aluminum-copper, mixtures of aluminum-silicon, stainless steel, zinc, tungsten, lead and stainless steel; semiconductors; and conductive polymers. In the apparatus of the present invention, to cope with a problem that the sublimate in the antireflection film scatters in the chamber and falling matters thereof cause generation of foreign matters by using measurement of the sublimate is considered. The main objects of the apparatus of the present invention are the improvement of the composition for forming an antireflection film and the temperature control during the thermosetting process by accurately determining the quantity of the sublimate in real time unlike the conventional method. Therefore, it is suitable for the purpose of the measurement to form beforehand an environment in which the scattered sublimate adhered. Thus, by coating the surface of the crystal oscillator with the same material as that of the chamber inner wall or the spinning coat film on the wafer, the determination of quantity of the concerned sublimate becomes more realistic. In addition, the surface of the crystal oscillator is coated with, preferably the same material as the surface material of the enclosure covering the thermoset film or a coating material forming the thermoset film, for example with compounds containing silicon and aluminum. In the apparatus of the present invention, even when the electrode part is the electrode described above, the surface state of the electrode can be improved by spin coating. For example, by using a compound containing silicon and aluminum in the composition of the electrode, the electrode may be coated beforehand with the same material as that of a top board of the actual apparatus, without using the same material as that of the top board of the actual apparatus or changing the electrode.

In addition, in the flow attachment (detection part), a transmitter for vibrating the crystal oscillator may be installed. This transmitter incorporates an inverter transmit circuit and is installed preferably near the sensor, and more preferably in a position departing from the sensor by 3 cm or less. Therefore, for the design, the transmitter is necessary to be installed inside the flow attachment or at a position outside but near the flow attachment. However, the installation manner may be any one of the both.

The pump unit is formed from a pump for generating the airstream and a flow rate controller for controlling the flow rate of the airstream. The airstream generated by the pump flows in through the flow attachment, in a state in which the flow rate thereof is controlled by the flow rate controller. At this time, the flow rate controller may be integrated with the pump.

The airstream is generated by the suction of the pump in a flow rate of 0.01 to 50 m$^3$/s which is controlled by the flow rate controller to 0.01 to 20.0 m³/s, more preferably 0.1 to 10.0 m³/s and the flow rate during one measurement is controlled constant.

The apparatus used in the present invention is necessary to have a display for confirming the change in the frequency, besides three units for generating the sublimate and collecting efficiently the sublimate. For the measurement in real time, a data processing for the display is performed using a personal computer. Therefore, a serial cable for the computer and a dedicated software are necessary. By attaching these parts, a continuous data analysis becomes possible and the errors can be reduced in comparison with a discontinuous data.

The measurement is performed with each unit fixed. At this time, it is necessary to maintain the hot plate, and the chamber unit and the flow attachment that are heated by the hot plate, at a constant temperature. For this purpose, after the hot plate has reached a predetermined measuring temperature, it is necessary to stabilize the temperature until the temperature of each unit becomes constant by operating the pump for controlling the flow rate. A change in the temperature can be confirmed on the display that enables continuous monitoring on the personal computer.

After the stabilization of the temperature, a wafer coated with a sample to be measured is introduced into the apparatus such that the change in the temperature during the installation is small. Then, the change in the frequency is confirmed on the personal computer. At this time, the temperature and the flow rate are always kept constant and such a state is maintained for a predetermined time.

Examples using the measuring apparatus are shown as follows.

EXAMPLES

Example 1

A silicon wafer substrate having a diameter of 4 inches was coated with a commercially available composition for forming an antireflection film by a spin coater at 2,500 rpm for 60 seconds. At that time, the antireflection film had a film thickness of 78 nm.

The above composition for forming an antireflection film (a composition for forming an antireflection film used in a lithography process for producing a semiconductor device) consists of a hydroxyl group-containing acrylic ester-based polymer (having a weight average molecular weight of 80,000), a crosslinkable compound (hexamethoxymethyl melamine), a crosslinking catalyst (p-toluenesulfonic acid) and a solvent (propyleneglycol monomethyl ether acetate and ethyl lactate), and had a solid content of 4.3% by mass.

The wafer coated with the antireflection film was set in a sublimate measuring apparatus integrated with a hot plate adjusted at 205° C. and was baked for 120 seconds to collect and determine the quantity of the sublimate by a QCM sensor.

For the measurement, the hot plate was heated to 205° C., the pump flow rate was set at 1 m³/s, and the apparatus was left to stand for first 60 seconds for aging. Immediately after that, a wafer coated with an antireflection film was swiftly placed on the hot plate through the sliding aperture (install the subject to be measured) and the collection of the sublimate was performed from the time point of 60 seconds to the time point of 180 seconds (for 120 seconds).

In addition, a nozzle having an aperture of 2 mm was attached to the flow attachment (detection part) which is a connection between the QCM sensor and the collecting funnel part, and the distance between the sensor and the nozzle was maintained at 0.5 mm. Further, used was a QCM sensor in which the electrode was composed of a compound containing silicon and aluminum; the crystal oscillator had a diameter (sensor diameter) of 14 mm and a resonance frequency of 9 MHz; and the electrode on the surface of the crystal oscillator had a diameter of 5 mm.

Example 2

A silicon wafer substrate having a diameter of 4 inches was coated with a commercially available composition for forming an antireflection film by a spin coater at 2,500 rpm for 60 seconds. At that time, the antireflection film had a film thickness of 35 nm.

The above composition for forming an antireflection film (a composition for forming an antireflection film used in a lithography process for producing a semiconductor device) consists of a hydroxyl group-containing triazine trione-based polymer (having a weight average molecular weight of 10,000), a crosslinkable compound (hexamethoxymethyl melamine), a crosslinking catalyst (p-toluenesulfonic acid) and a solvent (propyleneglycol monomethyl ether and propyleneglycol monomethyl ether acetate), and had a solid content of 1.9% by mass.

The wafer coated with the antireflection film was set in a sublimate measuring apparatus integrated with a hot plate adjusted at 205° C. and was baked for 120 seconds to collect and determine the quantity of the sublimate by the QCM sensor.

For the measurement, the hot plate was heated to 205° C., the pump flow rate was set at 1 m³/s, and the apparatus was left to stand for first 60 seconds for aging. Immediately after that, a wafer coated with an antireflection film was swiftly placed on the hot plate through the sliding aperture (install the substance to be measured) and the collection of the sublimate was performed from the time point of 60 seconds to the time point of 180 seconds (for 120 seconds).

In addition, a nozzle having an aperture of 2 mm was attached to the flow attachment (detection part) which is a connection between the QCM sensor and the collecting funnel part, and the distance between the sensor and the nozzle was maintained at 0.5 mm. Further, used was a QCM sensor in which the electrode was composed of a compound containing silicon and aluminum; the crystal oscillator had a diameter (sensor diameter) of 14 mm and a resonance frequency of 9 MHz; and the electrode on the surface of the crystal oscillator had a diameter of 5 mm.

Comparative Example 1

A silicon wafer substrate having a diameter of 4 inches was coated with the same composition for forming an antireflection film as that used in Example 1 by a spin coater at 2,500 rpm for 60 seconds. The wafer coated with the antireflection film was set in a sublimate measuring apparatus integrated with a hot plate adjusted at 205° C. and was baked for 120 seconds to collect the sublimate by the QCM sensor.

For the measurement, the hot plate was heated to 205° C., the pump flow rate was set at 0 m³/s (that is, in a state in which the airstream does not flow), and the apparatus was left to stand for first 60 seconds for aging. Immediately after that, a wafer coated with an antireflection film was swiftly placed on the hot plate through the sliding aperture (install the subject to be measured) and the collection of the sublimate was performed from the time point of 60 seconds to the time point of 180 seconds (for 120 seconds).

In addition, a nozzle having an aperture of 2 mm was attached to the flow attachment (detection part) which is a connection between the QCM sensor and the collecting funnel part, and the distance between the sensor and the nozzle was maintained at 0.5 mm. Further, used was a QCM sensor in which the electrode was composed of a compound containing silicon and aluminum; the crystal oscillator had a diameter (sensor diameter) of 14 mm and a resonance frequency of 9 MHz; and the electrode on the surface of the crystal oscillator had a diameter of 5 mm.

Comparative Example 2

A silicon wafer substrate having a diameter of 4 inches was coated with the same composition for forming an antireflection film as that used in Example 1 by a spin coater at 2,500 rpm for 60 seconds. The wafer coated with the antireflection film was set in a sublimate measuring apparatus integrated with a hot plate adjusted at 205° C. and was baked for 120 seconds to collect the sublimate by the QCM sensor.

For the measurement, the hot plate was heated to 205° C., the pump flow rate was set at 1 m$^3$/s, and the apparatus was left to stand for first 60 seconds for aging. Immediately after that, a wafer coated with an antireflection film was swiftly placed on the hot plate through the sliding aperture (install the subject to be measured) and the collection of the sublimate was performed from the time point of 60 seconds to the time point of 180 seconds (for 120 seconds).

In addition, a nozzle having an aperture of 20 mm was attached to the flow attachment (detection part), and the distance between the sensor and the nozzle was maintained at 0.5 mm. Further, used was a QCM sensor in which the electrode was composed of a compound containing silicon and aluminum; the crystal oscillator had a diameter (sensor diameter) of 14 mm and a resonance frequency of 9 MHz; and the electrode on the surface of the crystal oscillator had a diameter of 5 mm.

Comparative Example 3

A silicon wafer substrate having a diameter of 4 inches was coated with the same composition for forming an antireflection film as that used in Example 1 by a spin coater at 2,500 rpm for 60 seconds. The wafer coated with the antireflection film was set in a sublimate measuring apparatus integrated with a hot plate adjusted at 205° C. and was baked for 120 seconds to collect the sublimate by the QCM sensor.

For the measurement, the hot plate was heated to 205° C., the pump flow rate was set at 1 m$^3$/s, and the apparatus was left to stand for first 60 seconds for aging. Immediately after that, a wafer coated with an antireflection film was swiftly placed on the hot plate through the sliding aperture (installation of substance to be measured) and the collection of the sublimate was performed from the time point of 60 seconds to the time point of 180 seconds (for 120 seconds).

In addition, to the flow attachment (detection part), a nozzle was not attached, so that the aperture was 32 mm and the airstream flowed into the flow attachment through the flow path between the sensor and the chamber unit departing from the sensor by 30 mm, without being narrowed down. Further, used was a QCM sensor in which the electrode was aluminum silicon material; the crystal oscillator had a diameter (sensor diameter) of 14 mm and a resonance frequency of 9 MHz; and the electrode on the surface of the crystal oscillator had a diameter of 5 mm.

Comparative Example 4

A silicon wafer substrate having a diameter of 4 inches was coated with the same composition for forming an antireflection film as that used in Example 2 by a spin coater at 2,500 rpm for 60 seconds. The wafer coated with the antireflection film was set in a sublimate measuring apparatus integrated with a hot plate adjusted at 205° C. and was baked for 120 seconds to collect the sublimate by the QCM sensor.

For the measurement, the hot plate was heated to 205° C., the pump flow rate was set at 0 m$^3$/s (that is, in a state in which the airstream does not flow), and the apparatus was left to stand for first 60 seconds for aging. Immediately after that, a wafer coated with an antireflection film was swiftly placed on the hot plate through the sliding aperture (install the subject to be measured) and the collection of the sublimate was performed from the time point of 60 seconds to the time point of 180 seconds (for 120 seconds).

In addition, a nozzle having an aperture of 2 mm was attached to the flow attachment (detection part) which is a connection between the QCM sensor and the collecting funnel part, and the distance between the sensor and the nozzle was maintained at 0.5 mm. Further, used was a QCM sensor in which the electrode was composed of a compound containing silicon and aluminum; the crystal oscillator had a diameter (sensor diameter) of 14 mm and a resonance frequency of 9 MHz; and the electrode on the surface of the crystal oscillator had a diameter of 5 mm.

Comparative Example 5

A silicon wafer substrate having a diameter of 4 inches was coated with the same composition for forming an antireflection film as that used in Example 2 by a spin coater at 2,500 rpm for 60 seconds. The wafer coated with the antireflection film was set in a sublimate measuring apparatus integrated with a hot plate adjusted at 205° C. and was baked for 120 seconds to collect the sublimate by the QCM sensor.

For the measurement, the hot plate was heated to 205° C., the pump flow rate was set at 1 m$^3$/s, and the apparatus was left to stand for first 60 seconds for aging. Immediately after that, a wafer coated with an antireflection film was swiftly placed on the hot plate through the sliding aperture (install the subject to be measured) and the collection of the sublimate was performed from the time point of 60 seconds to the time point of 180 seconds (for 120 seconds).

In addition, a nozzle having an aperture of 20 mm was attached to the flow attachment (detection part), and the distance between the sensor and the nozzle was maintained at 0.5 mm. Further, used was a QCM sensor in which the electrode was composed of a compound containing silicon and aluminum; the crystal oscillator had a diameter (sensor diameter) of 14 mm and a resonance frequency of 9 MHz; and the electrode on the surface of the crystal oscillator had a diameter of 5 mm.

Comparative Example 6

A silicon wafer substrate having a diameter of 4 inches was coated with the same composition for forming an antireflection film as that used in Example 2 by a spin coater at 2,500 rpm for 60 seconds. The wafer coated with the antireflection film was set in a sublimate measuring apparatus integrated with a hot plate adjusted at 205° C. and was baked for 120 seconds to collect the sublimate by the QCM sensor.

For the measurement, the hot plate was heated to 205° C., the pump flow rate was set at 1 m$^3$/s, and the apparatus was left to stand for first 60 seconds for aging. Immediately after that, a wafer coated with an antireflection film was swiftly placed on the hot plate through the sliding aperture (install the subject to be measured) and the collection of the sublimate was performed from the time point of 60 seconds to the time point of 180 seconds (for 120 seconds).

In addition, a nozzle was not attached to the flow attachment (detection part), so that the aperture was 32 mm and the airstream flowed into the flow attachment through the flow path between the sensor and the chamber unit departing from the sensor by 30 mm, without being narrowed down. Further, used was a QCM sensor in which the electrode was composed of aluminum silicon material; the crystal oscillator had a diameter (sensor diameter) of 14 mm and a resonance frequency of 9 MHz; and the electrode on the surface of the crystal oscillator had a diameter of 5 mm.

In each measurement of Examples 1 and 2 and Comparative Examples 1 to 6, in order for the QCM sensor to measure the sublimate in real time, the connection of a serial cable and the installation of dedicated software for capturing the data directly into the personal computer were performed.

The obtained frequency change was converted into the weight in grams from the eigenvalue of the crystal oscillator used for the measurement, and the graph of the sublimate amount in one piece wafer coated with the antireflection film vs. the lapsed time was described.

In FIGS. 1 and 2, the sublimate amount (unit: ng) from 0 second to 180 seconds shown by the measuring apparatuses in Examples 1 and 2 and Comparative Examples 1 to 6 is described. In other words, there are shown the aging time (untreated time) from the time point of 0 second to the time point of 60 seconds and the measured value of the sublimate from the time point of 60 seconds to the time point of 180 seconds.

In addition, FIGS. 5 to 12 show graphs of the above lapsed time and the amount of sublimate in Examples 1 and 2 and Comparative Examples 1 to 6.

[Table 1]

TABLE 1

Sublimate amount shown by measuring apparatus (ng)

| Lapsed time (sec) | Example 1 | Comparative Example 1 | Comparative Example 2 | Comparative Example 3 |
|---|---|---|---|---|
| 0 sec | 45 | −6 | 12 | 1 |
| 30 sec | 11 | 5 | −2 | −2 |
| 60 sec | 102 | 14 | 76 | 31 |
| 90 sec | 594 | 21 | 111 | 15 |
| 120 sec | 708 | 26 | 121 | 22 |
| 150 sec | 748 | 31 | 141 | 28 |
| 180 sec | 817 | 34 | 146 | 24 |

TABLE 2

Sublimate amount shown by measuring apparatus (ng)

| Lapsed time (sec) | Example 2 | Comparative Example 4 | Comparative Example 5 | Comparative Example 6 |
|---|---|---|---|---|
| 0 sec | 5 | 6 | −2 | 3 |
| 30 sec | −19 | 13 | −5 | −15 |
| 60 sec | 209 | 18 | 49 | −30 |
| 90 sec | 468 | 22 | 36 | 1 |
| 120 sec | 534 | 26 | 49 | 14 |
| 150 sec | 587 | 29 | 52 | 9 |
| 180 sec | 630 | 31 | 61 | 9 |

Tables 1 and 2 and the figures corresponding thereto show the sublimate amount indicated by the measuring apparatus for showing a stable state of the measuring apparatus in a state where the measuring apparatus does not yet measure the sublimate from the time point of 0 sec to the time point of 60 sec. Thus, the value with minus was read as it is.

In the methods of Examples 1 and 2, for the initial aging time (untreated time), the value shown by the measuring apparatus was stable and it could be observed that after the aging time, the adhered amount of the sublimate increased along with the measuring time.

When Example 1 and Example 2 are compared to each other, the sublimate amounts can be relatively compared. Thus, by coating the subject to be measured on the wafer and by measuring the sublimate amount with the measuring apparatus of the present invention on the same condition, the respective sublimate amounts of the subjects to be measured can be relatively discriminated. In other words, when Example 1 and Example 2 are compared to each other, it is apparent that the sublimate amount of the composition for forming the antireflection film in Example 2 is more suppressed than that in Example 1. In addition, in the relative comparison, by taking into consideration the solid content in the composition forming the subject to be measured and the film thickness of the subject to be measured on the wafer, more accurate comparison becomes possible.

On the other hand, though the subjects to be measured in Comparative Examples 1 to 3 are the same as that in Example 1 and the subjects to be measured in Comparative Examples 4 to 6 are the same as that in Example 2, the difference in the sublimate amount between Comparative Example 1 and Comparative Example 4, between Comparative Example 2 and Comparative Example 5 and between Comparative Example 3 and Comparative Example 6 is not so distinct as the difference in the sublimate amount between Example 1 and Example 2. In addition, in Comparative Examples, a change in the measured value at each measuring time was small, so that the judgment of the change in the sublimate amount with time is difficult.

INDUSTRIAL APPLICABILITY

It is useful for the development of a composition for forming an antireflection film or a composition for forming a resist film which generate no sublimate or a slight amount of the sublimate, to detect the presence or absence, or the amount of sublimate generated during thermosetting of a thermoset film such as a composition for forming an antireflection film or composition for forming a resist film.

Further, by detecting the amount of the sublimate that is generated with the lapse of heating time, it is useful for investigating a temperature elevation process which is unlikely to generate the sublimate when coating a composition for forming an antireflection film or composition for forming a resist film and thermosetting them by heating.

The invention claimed is:

1. A method for measuring an amount of a sublimate in real time with respect to a lapse of heating time, the method comprising:
    adhering the sublimate from a thermoset film during heating to a surface of a crystal oscillator using a nozzle inserted into a detection part; and
    measuring the amount of the sublimate from a change in a resonance frequency corresponding to the amount of the sublimate adhered to the crystal oscillator.

2. The method according to claim 1, wherein the thermoset film is formed on a silicon wafer and the measurement is performed while the thermoset film is heated by a heat source disposed under the silicon wafer.

3. The method according to claim 1, wherein the sublimate is set so as to flow together with an airstream ascending toward an upper part of an enclosure covering the thermoset film, and the airstream directly contacts the crystal oscillator through the nozzle inserted into the detection part disposed in the path of the airstream.

4. The method according to claim 1, wherein the airstream is generated by the suction of a pump and a flow rate thereof is 0.01 to 20.0 m3/s.

5. The method according to claim 1, wherein the nozzle inserted into the detection part has a nozzle aperture smaller than the diameter of a sensor and a distance between the nozzle and the sensor is shorter than the diameter of the sensor.

6. The method according claim 1, wherein the heat source is that controlled to temperatures of 100 to 400° C. by a hot plate.

7. The method according to claim 1, wherein the surface of the crystal oscillator is coated with a material identical to a surface material of the enclosure covering the thermoset film or with a coating material forming the thermoset film.

8. The method according to claim 7, wherein the coating of the surface of the crystal oscillator is a compound containing silicon and aluminum.

9. The method according to claim 1, wherein the crystal oscillator is used at a resonance frequency ranging from 100 Hz to 100 MHz.

10. The method according claim 1, wherein the thermoset film is an antireflection film used as an under layer of a photoresist used in a lithography process for producing a semiconductor device.

11. An apparatus for measuring a sublimate from a thermoset film utilizing the method as claimed in claim 1.

* * * * *